United States Patent
Ylikomi et al.

(10) Patent No.: US 9,056,084 B2
(45) Date of Patent: Jun. 16, 2015

(54) METHODS AND MEANS FOR SOFT TISSUE ENGINEERING

(76) Inventors: Timo Ylikomi, Karkku (FI); Jertta-Riina Sarkanen, Kangasala (FI)

( * ) Notice: Subject to any disclaimer, the term of this patent is extended or adjusted under 35 U.S.C. 154(b) by 12 days.

(21) Appl. No.: 13/040,957

(22) Filed: Mar. 4, 2011

(65) Prior Publication Data

US 2011/0151005 A1 Jun. 23, 2011

Related U.S. Application Data

(63) Continuation of application No. PCT/FI2009/050715, filed on Sep. 7, 2009.

(60) Provisional application No. 61/095,198, filed on Sep. 8, 2008.

(30) Foreign Application Priority Data

Sep. 8, 2008 (FI) ...................................... 20085839

(51) Int. Cl.
*A61K 9/14* (2006.01)
*A61K 35/12* (2006.01)
*A61P 17/02* (2006.01)
*A61P 9/10* (2006.01)
*C12N 5/00* (2006.01)
*C12P 21/00* (2006.01)
*A61K 38/18* (2006.01)
*A61K 38/30* (2006.01)
*A61L 27/36* (2006.01)
*A61L 27/52* (2006.01)

(52) U.S. Cl.
CPC ......... *A61K 38/1866* (2013.01); *A61K 38/1825* (2013.01); *A61K 38/30* (2013.01); *A61L 27/3604* (2013.01); *A61L 27/52* (2013.01); *A61K 35/35* (2013.01)

(58) Field of Classification Search
USPC .......... 424/486, 484, 488, 574; 435/405, 70.3
See application file for complete search history.

(56) References Cited

U.S. PATENT DOCUMENTS

2006/0153797 A1 * 7/2006 Bortolotto et al. ........... 424/85.1

FOREIGN PATENT DOCUMENTS

| WO | 2005/011569 A2 | | 2/2005 |
|---|---|---|---|
| WO | WO 2006/029262 | * | 3/2006 |
| WO | WO 2006/029262 A2 | | 3/2006 |
| WO | WO 2008/041909 A1 | | 4/2008 |
| WO | WO 2009/102452 A2 | | 8/2009 |

OTHER PUBLICATIONS

Fu et al. Adipose Tissue Extract Enhances Skin Wound Healing, Wound Repair and Regeneration, Jul.-Aug. 2007, 15 (4), 540-548 (Abstract only).*
International Search Report (PCT/ISA/210) issued on Nov. 11, 2009, by Finish Patent Office as the International Searching Authority for International Application No. PCT/FI2009/050715.
Japanese Office Action dated Sep. 27, 2013, issued in the corresponding Japanese Patent Application No. 2011-525584, and an English Translation thereof . ( 6 pgs).

* cited by examiner

*Primary Examiner* — Gina Justice
*Assistant Examiner* — Genevieve S Alley
(74) *Attorney, Agent, or Firm* — Buchanan Ingersoll & Rooney PC

(57) ABSTRACT

Cellfree adipose tissue extracts, implants including the same and methods for the preparation thereof. The extracts and implants are capable of inducing adipogenesis and angiogenesis and are, thus, useful in applications including soft tissue repair and engineering and angiogenesis induction, e.g., in wound healing, treatment of burn injuries and ischemic conditions.

20 Claims, 6 Drawing Sheets

METHODS AND MEANS FOR SOFT TISSUE ENGINEERING

RELATED APPLICATIONS

This application is a continuation application under 35 U.S.C. §120 of PCT/FI2009/050715 filed as an International Application on Sep. 7, 2009 designating the U.S., which claims priority to Finnish Application No. 20085839 filed in Finland on Sep. 8, 2008, and which claims the benefit under 35 U.S.C. §119 of U.S. Provisional Patent No. 61/095,198 filed on Sep. 8, 2008, the entire contents of which are hereby incorporated by reference in their entireties.

FIELD

The present disclosure relates to soft tissue engineering. For example, the present disclosure is directed to an acellular adipose tissue extract, an implant including the extract, methods for their preparation and uses thereof.

BACKGROUND INFORMATION

Soft tissue includes connecting and supporting structures in the body, for example, muscles, connective tissue, adipose tissue and blood vessels. Soft tissue engineering seeks to fabricate replacement parts for soft tissue defects resulting from, e.g., trauma (burns and scars), surgical resection or congenital malformations. In addition, cosmetic use, such as filling of facial wrinkles, is an important application of reconstituted soft tissue.

Alloplastic materials, such as silicon and bovine collagen, have been used in tissue engineering. Such materials may, however, cause severe rejection reactions, as well as allergic reactions. Thus, the use of natural transplant materials is nowadays preferred.

Autologous transplants would be desirable for use in soft tissue engineering. Autologous adipose tissue transplantation is an old therapeutic procedure, where mature adipocytes or adipose tissue itself are transplanted into the site of defect. Adipose tissue is abundant, easy to collect, and readily obtainable for clinical uses. However, the use of autologous adipose tissue transplants may still result in several problems such as resorption, excessive connective tissue (scar) formation, inflammation reactions, as well as hardening and clotting of the transplant. Furthermore, long-term results obtained with adipose tissue transplantation are unpredictable and variable, depending on the method used and the skills of the person executing the method.

Adipose stem cells have been used for soft tissue engineering. Such cells are capable of proliferating and differentiating into mature adipose tissue. However, as the extracellular matrix has an essential role in cell proliferation and differentiation, it is unlikely that repair of large or deep soft tissue defects would be possible with cells alone. In order to be regenerated into functional tissue, transplanted cells need an artificial extracellular matrix, i.e. biomaterial scaffold to aid in cell attachment, proliferation and differentiation.

Formation of new blood vessels, i.e. neovascularization, is crucial for nutrient supply and waste disposal in the regenerating soft tissue. To date, single growth factors (e.g. FGF-2 or VEGF) have been used as bioactive substances for this purpose, but the results have not been satisfactory. It appears that there is a need for a pool of different growth/differentiation factors instead of single factors merely. The right combination of differentiation factors is, however, unknown. Using a pool of bioengineered growth factors in a single implant may result in very high costs.

To date, no adequate approach to the reconstruction of soft tissue defects is available. Thus, there is an acknowledged need in the art to develop implants that induce a rapid volumetric gain to fill defects, maintain the transplanted tissue with no time-dependent volumetric loss, and induce rapid neovascularization.

SUMMARY

According to an exemplary embodiment, the present disclosure provides a cellfree adipose tissue extract, including a predetermined amount of VEGF, FGF-2, and IGF-1.

According to an exemplary embodiment, the present disclosure provides an implant including a cellfree adipose tissue extract, including a predetermined amount of VEGF, FGF-2, and IGF-1, and a biocompatible matrix.

According to an exemplary embodiment, the present disclosure provides a method of preparing a cellfree adipose tissue extract including a predetermined amount of VEGF, FGF-2, and IGF-1, the method including the following steps: a) providing a non-homogenized adipose tissue sample including viable cells, b) incubating the sample a predetermined time, and c) collecting the extract.

According to an exemplary embodiment, the present disclosure provides a cellfree adipose tissue extract obtained by the method of preparing a cellfree adipose tissue extract including a predetermined amount of VEGF, FGF-2, and IGF-1, the method including the following steps: a) providing a non-homogenized adipose tissue sample including viable cells, b) incubating the sample a predetermined time, and c) collecting the extract.

According to an exemplary embodiment, the present disclosure provides a method of preparing an implant including a cellfree adipose tissue extract, including a predetermined amount of VEGF, FGF-2, and IGF-1, and a biocompatible matrix, the method including mixing the adipose tissue extract with, or absorbing the same into, the biocompatible material.

According to an exemplary embodiment, the present disclosure provides a method of inducing adipogenesis, the method including implanting into a subject in need thereof an implant including a cellfree adipose tissue extract, including a predetermined amount of VEGF, FGF-2, and IGF-1, and a biocompatible matrix.

According to an exemplary embodiment, the present disclosure provides a method of inducing angiogenesis, the method including implanting into a subject in need thereof an implant including a cellfree adipose tissue extract, including a predetermined amount of VEGF, FGF-2, and IGF-1, and a biocompatible matrix.

BRIEF DESCRIPTION OF THE DRAWINGS

In the following, the present disclosure will be described in greater detail by means of exemplary embodiments and with reference to the attached drawings, in which FIG. 1A shows the total protein concentration in 20 randomly selected human adipose tissue extracts at different time points. FIGS. 1B, 1C, and 1D show the concentrations of IGF-1, FGF-2 and VEGF, respectively, in human adipose tissue extracts (ATE) at different time points. A mean is shown as a bar in each figure.

FIG. 2A shows hASCs grown in a control growth medium. FIG. 2B shows hASCs growing in an ATE medium containing about 350 µg/ml protein, FIG. 2C about 700 µg/ml protein, and FIG. 2D about 1200 µg/ml of protein. ATE treatments have dose-dependent potential of adipogenesis induction.

FIG. 3A represents a negative control showing no tube formation. FIGS. 3B and 3C represent cells treated with 900 µg/ml (protein content) or 1300 µg/ml of ATE, respectively. FIG. 3D shows positive control cells, treated with known angiogenic growth factors, 10 ng/ml of VEGF and 1 ng/ml of FGF-2. Tube formation can be clearly seen in FIGS. 3B, 3C, and 3D. Both ATE treatments have equal but dose-dependent potential of angiogenesis induction as compared to the angiogenic potential of the positive control 3D.

FIGS. 4A and 4B show extensive capillary formation in the implant area. FIGS. 4C and 4D show large arteriole-like structures as well as some adipose tissue development. Examples of vessels are shown by arrows.

FIG. 6A shows the tissue before implantation. FIG. 6B shows the subcutis at three months after implantation. FIG. 6C shows upper subcutis vessel formation at six months. FIG. 6D shows the adipose tissue and vascularization in the subcutis just below the dermis at six months. The tissue mass has at least doubled at six months, and adipose tissue and large vessels have developed.

DETAILED DESCRIPTION

Figure 1A:
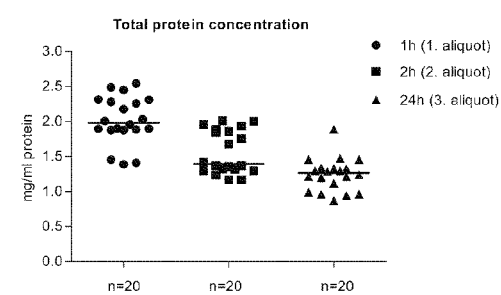
FIGS. 1A-1D illustrate total protein and growth factor contents in adipose tissue extracts according to the present disclosure.

De novo adipogenesis is a promising approach to soft tissue engineering. The present disclosure is based on studies attempting to provide a microenvironment that is suitable for cell proliferation and differentiation, thus resulting in formation of adipose tissue without exogenous transplantation of cells. An optimal microenvironment enhances migration of adipose stem cells from the surrounding tissue and induces the cells to differentiate into mature adipocytes. Neovascularization in the developing tissue is used to avoid necrosis, scar formation and resorbtion of transplanted tissue, as well as to secrete several differentiation factors.

The present disclosure provides a cellfree adipose tissue extract, including a predetermined amount of VEGF, FGF-2, and IGF-1. In an exemplary embodiment, the extract includes at least 1 pg of VEGF, at least 70 pg of FGF-2, and at least 50 pg of IGF-1 per 1 mg of total protein. In an exemplary embodiment, the VEGF content per 1 mg of total protein is at least 7 pg. The extract may be used in soft tissue repair or engineering and in angiogenesis induction in tissue engineering, e.g., in wound healing, in treating burn injuries and in treating ischemic conditions.

The present disclosure further provides an implant including a cellfree adipose tissue extract according to any embodiment of the present disclosure and a biocompatible matrix. The extract may be, for example, allogenic, whereas the matrix is, for example, a hydrogel and may be selected from a group consisting of hyaluronic acid, chitosan, fibrin, collagen, alginate, polyesters based on poly lactic acid, poly lactic glycolic acid, polycaprolactone, and mixtures thereof. In an exemplary embodiment, the implant is injectable. The implant may be used in soft tissue repair or engineering and in angiogenesis induction in tissue engineering, e.g., in wound healing, in treating burn injuries and in treating ischemic conditions.

The present disclosure still further provides a method of preparing a cellfree adipose tissue extract according to any embodiment of the present disclosure. The method includes the steps of a) providing a non-homogenized adipose tissue sample including viable cells, b) incubating the sample a predetermined time, and c) collecting the extract. Further provided is the cellfree adipose tissue extract obtainable by the method.

Furthermore, the present disclosure provides a method of preparing an implant according any embodiment of the present disclosure. The method includes mixing the adipose tissue extract with, or absorbing the same into, a biocompatible material.

Still further, the present disclosure provides a method of inducing adipogenesis and a method of inducing angiogenesis. The methods include implanting into a subject in need thereof an implant according to any appropriate embodiment of the present disclosure.

Adipose tissue includes adipocytes of various differentiation states, endothelial cells, fibroblasts, pericytes as well as adipose stem cells and mesenchymal stem cells that are capable of differentiating into several lineages of cells. De novo adipogenesis, i.e. formation of new adipose tissue, is a promising approach to soft tissue engineering. The present disclosure is based on studies attempting to provide a microenvironment that is suitable for cell proliferation and differentiation, thus resulting in formation of blood vessels and adipose tissue without exogenous transplantation of cells. An optimal microenvironment enhances migration of adipose stem cells from the surrounding tissue and induces differentiation of endothelial and adipocyte precursor cells into mature adipocytes, loose connective tissue and muscle cells and vascular cells. Neovascularization in the developing tissue is used to avoid necrosis and scar formation, i.e. in order to enable the functional mature adipose tissue to develop.

The present disclosure relates to a cellfree adipose tissue extract (ATE) having potential for inducing rapid formation of adipose tissue and vasculature at the site of implantation without administration of cells. The ATE is capable of creating an optimal microenvironment for de novo adipogenesis and angiogenesis and may thus be used in soft tissue repair and/or engineering.

The term "adipose tissue extract" (ATE) herein refers to a mixture of bioactive substances, for example, adipogenic and angiogenic factors, secreted by the adipose tissue cells, for example, adipocytes of various differentiation states, endothelial cells, fibroblasts, pericytes as well as adipose stem cells. The extract is cellfree or acellular. The adipose tissue extract differs from a traditional conditioned medium, for instance, in that the extract is collected from small tissue pieces or viable cells. The preparation process includes no cell culturing, the resulting extract is much more concentrated than a conditioned medium, and the incubation time is short varying from several minutes to a couple of days.

Adipose tissue extract may be prepared from fat or adipose tissue sample obtained, e.g., from liposuction or a surgical operation. If necessary, the tissue sample is cut into small pieces such that the cells remain substantially viable. Liposuction material may be used directly. In other words, processing of the tissue sample does not involve homogenization. The bioactive factors are extracted by incubating cells in a culture medium, in a sterile salt solution, for example, in a phosphate buffered saline or in other suitable isotonic aqueous buffer solutions where cells or tissue pieces release bioactive factors into the liquid phase during incubation. The ATE, i.e. liquid phase without cells is then collected. The ATE may also be filtered prior to use to sterilize the extract and to create acellular liquid. The resulting ATE is a cell-free protein mixture of cytokines and other bioactive substances.

Not only autologous, but also allogenic adipose tissue may be used as a source of an ATE, and processed to that end as described above. Such allogenic extracts could be absorbed into and used in, e.g., freeze-dried "off-the-shelf" soft tissue scaffolds. One example of a product of this kind is made from crosslinked hyaluronic acid (e.g. Restylane) and allogenic ATE. Since the extract is acellular, immune responses and allergic reactions are unlikely even in allogenic use where the same extract and implant suits several patients. This is supported by animal studies described in more detail in Example 5, where human ATE implanted in rats (xenograft) did not cause any inflammation reactions or other complications.

ATE is an optimal cytokine mixture of adipogenic and angiogenic factors that are expressed by the cells of adipose tissue. Bioactive substances of ATE may be measured by routine methods known in the art (e.g. ELISA). Herein, expression of 120 cytokines in various ATEs was measured (see Example 1). Long incubation time, such as 24 hours or more, resulted in a more angiogenic extract, whereas both short and long incubation times produced an adipogenic mixture.

An ATE may be tailored to include desired, or predetermined, amounts of adipogenic and angiogenic factors, including a vascular endothelial cell growth factor (VEGF), basic fibroblast growth factor (FGF-2), and insulin-like growth factor (IGF-1). The desired composition may depend on the intended use. According to the current knowledge and supported by the present disclosure, VEGF and FGF-2 are regarded as known factors for stimulating angiogenesis, whereas FGF-2 and IGF are known for stimulating adipogenesis. Thus, in an exemplary embodiment the ATE includes at least 1 pg of VEGF, at least 70 pg of FGF-2, and at least 50 pg of IGF-1 per 1 mg of total protein. Such an ATE is particularly suitable for stimulating adipogenesis, e.g., in soft tissue repair and engineering. In an exemplary embodiment, the ATE includes at least 7 pg of VEGF, at least 70 pg of FGF-2, and at least 50 pg of IGF-1 per 1 mg of total protein. This kind of an ATE is particularly useful in stimulating angiogenesis, e.g., in inducing wound healing and treating ischemic conditions and burn injuries. Different tailored ATEs may further contain different amounts of several other cytokines although they may not always be crucial for the specific application (see Table 1). In general, ATE should contain about 2:1 to about 1:2 IGF-1 and FGF-2, and about 1:100 to about 1:10 VEGF and FGF-2.

The content of an adipose tissue extract may be tailored by using different incubation times and temperatures in the preparation of the ATE. In an exemplary embodiment, the incubation time ranges from a few minutes to several hours, such as overnight. In an exemplary embodiment, an incubation time of about 1 hour may result in a total protein content of about 1.7 mg/ml to about 2.5 mg/ml, IGF-1 content of about 200 pg/ml to about 1300 pg/ml, FGF-2 content of about 200 pg/ml to about 1400 pg/ml, and VEGF content of about 2 pg/ml to about 25 pg/ml. In an exemplary embodiment, incubation time of 1 hour may result in IGF-1 content of about 150 pg to about 550 pg per 1 mg of total protein, in FGF-2 content of about 100 pg to about 500 pg per 1 mg of total protein, and in VEGF content of about 3 pg to about 20 pg per 1 mg of total protein. This type of extract is both adipogenic and angiogenic. If, however, an especially high concentration of VEGF (about 200 pg/ml to about 1400 pg/ml, that is about 25 pg to about 500 pg of VEGF per 1 mg of protein) is desirable in the extract, e.g., especially for angiogenesis induction in the desired target tissue, the incubation time should be extended, e.g., to about 24 hours. In an exemplary embodiment, incubation time of 24 hour may result in IGF-1 content of about 60 pg to about 200 pg per 1 mg of total protein, in FGF-2 content of about 130 pg to about 500 pg per 1 mg of total protein, and in VEGF content of about 25 pg to about 500 pg per 1 mg of total protein. In an exemplary embodiment, various incubation temperatures, ranging from room temperature to about 37° C., may be used to modify the adipose tissue extract. In an exemplary embodiment, lower temperatures such as 4° C. may be used. In an exemplary embodiment, higher temperatures may be used as long as the proteins will not denaturate.

In an exemplary embodiment, the concentration of VEGF in the extract may vary between about 1 pg/ml and about 1400 pg/ml, and, for example, between about 10 pg/ml to about 1000 pg/ml, for example, between about 7 pg/ml to about 700 pg/ml, and for example, between about 10 pg/ml to about 100 pg/ml. For example, the concentration of FGF-2 in the extract may vary between about 20 pg/ml to about 1500 pg/ml, for example, between about 100 pg/ml to about 1300 pg/ml, for example, between about 150 pg/ml to about 1000 pg/ml, and for example, between about 200 pg/ml to about 800 pg/ml. In an exemplary embodiment, the concentration of IGF-1 may vary between about 100 pg/ml to about 1500 pg/ml, and for example, between about 150 pg/ml to about 800 pg/ml, and for example, between about 200 pg/ml to about 500 pg/ml. In an exemplary embodiment, the total protein concentration of the extract may vary between about 0.75 mg/ml and about 3.5 mg/ml. For example, the total protein concentration may be about 1.4 mg/ml to about 2.7mg/ml, for example, about 1.8 mg/ml to about 2.7 mg/ml, and for example, about 2 mg/ml to about 2.7 mg/ml, and for example, about 2.1 mg/ml to about 2.5 mg/ml.

The concentrations of the bioactive substances in the extract may also be defined in relation to the total protein concentration. Accordingly, in an exemplary embodiment, the amount of VEGF in an extract containing 1 mg of total protein (growth factor content per 1 mg of protein) may vary between about 1 pg and about 800 pg, and for example, between about 3.5 pg to about 500 pg, for example between about 7 pg to about 300 pg, and for example, between about 20 pg to about 100 pg. In an exemplary embodiment, the amount of FGF-2 in an extract containing about 1 mg of total protein (growth factor content per 1 mg of protein) may vary between about 1 pg to about 1200 pg, for example, between about 1 pg and about 600 pg, for example, between about 70 pg to about 500 pg, and for example, between about 110 pg to about 450 pg, and for example, between about 250 pg to about 350 pg. In an exemplary embodiment, the amount of IGF-1 (growth factor content per 1 mg of protein) may vary between about 50 pg to about 700 pg, and for example, between about 100 pg to about 500 pg, and for example, between about 100 pg to about 300 pg, and for example, between about 110 pg to about 230 pg.

In an exemplary embodiment, an ATE may further include several other adipogenic and angiogenic factors (presented in Table I) such as growth factors, interleukins, complement system products, glucocorticoids, prostaglandins, lipoproteins and free fatty acids as well as extracellular matrix components, e.g., collagen I, collagen IV and collagen VI, proteoglycans, elastin and hyaluronan either naturally or as added thereto to further tailor the ATE. In an exemplary embodiment, the ATE may be supplemented, for instance, with any desired drugs or medicaments prior to use.

In an exemplary embodiment, an ATE may be further tailored by removing substances, such as single growth factors or cytokines, prior to use. For example, inhibitors of angiogenesis, such as TIMP-1 and TIMP-2, and primarily adipogenic factors such as IGF-I, adiponectin and/or leptin may be removed if the ATE is to be used for inducing primarily angiogenesis, e.g., in treating ischemic conditions. Methods of removing or isolating desired substances are readily available in the art, including isolation of growth factors by immunoabsorption.

Tailoring an ATE may further include concentrating (e.g., by centrifugation) or diluting (e.g., with a culture medium, sterile physiological salt solution or any other buffered isotonic solution) in order to achieve a suitable ATE for a particular use.

The adipogenic potential of the adipose tissue extract was tested in cell culture studies, where human adipose derived stem cells (hASC) were cultured in the presence or absence of the extract according to the present embodiments. As demonstrated in FIGS. 2A-2D and described in more detail in Example 2, the extract clearly induced adipogenic differentiation of the majority of stem cell as judged by increased oil-red-O color accumulation (triglyseride formation).

Furthermore, the angiogenic potential of the extract according to the present embodiments was assessed in a tubule formation assay in vitro. Human endothelial cells were cultured on top of a fibroblast culture in the presence or absence of the adipose tissue extract, or VEGF and FGF-2. In all of the cases, angiogenesis, i.e. tube formation, was observed as demonstrated in FIGS. 3A-3D and described in more detail in Example 3. However, the angiogenic potential of the ATE was dose dependent.

In an exemplary embodiment, an ATE according to the present disclosure may be used as a cell culture medium or cell culture medium supplement to study adipogenesis or angiogenesis in vitro. The ATE results in even distribution of differentiated adipose cells in a cell culture and, thus, provides an excellent cell model for adipogenesis reflecting in vivo conditions in humans. To date, no adequate cell model for adipogenic differentiation exists.

There is a general objective to replace xenogenic serum in cell culturing, especially in clinical applications. Human serum is expensive and thus not an optimal solution. In an exemplary embodiment of the present disclosure, an ATE may be used as a cell culture component or as a serum substitute in a cell culture medium. This is not only cost-effective but useful for generating tissue engineered human constructs, especially when animal derived components are not suitable.

The present disclosure further relates to an implant including an autologous or allogenic cellfree adipose tissue extract and a biocompatible matrix. Repair of large or deep soft tissue defects is difficult with the adipose tissue extract alone, but the implant provided is suitable for filling the soft tissue defect, stands mechanical load, and also allows new tissue to be regenerated. Furthermore, the implant provides stable long-term results, feels and looks like a natural tissue, is easy to use, is nontoxic and inert but, on the other hand, allows adequate diffusion of nutrients and metabolites. The biocompatible matrix is, for example, non-toxic to humans, fairly inert in a tissue, able to bind and release small molecules (e.g. growth factors), and degradable in a tissue.

Biocompatible matrices used in the implant according to the present disclosure are, for example, hydrogels. The term "hydrogel" as used herein means a highly hydrated material which has hydrophilic polymer chains, is able to absorb water into its structure, swells hundreds or thousands percents of its original volume and still retains its structure. Natural polymer hydrogels have several promising properties. They are degradable, they can be processed in mild conditions and they either are components of the extracellular matrix (ECM) or have structural similarities therewith. Natural polymers are often non-toxic and interact well with the surrounding tissue in vivo. Hydrogel stiffness or rigidity, degradation rate, and bioactive substance binding or substance re-lease rate can be modified, depending on the demands of a specific implant. Methods for such modifications are readily available in the art.

One suitable hydrogel material is hyaluronic acid, or hyaluronan, which is a widely distributed natural polysaccharide that forms the extracellular matrix of connective tissues. It consists of groups of D-glucuronic acid linked to N-acetylglucosamine chains. Hyaluronic acid is a commonly used natural biomaterial since it is quite nonimmunogenic and has been used safely for several decades in the field. Crosslinked hyaluronic acid is commercially available, e.g., under the trade names Restylane® (Q-Med, Sweden), Elevess® (Anika Therapeutics, USA), Juvederm® (L.E.A. Derm, France), Reyoungel® (Bioha laboratories, China), Puragen® (Genzyme, USA), Prevelle Silk® (Genzyme, USA), Teosyal® (Teoxane laboratories, Switzerland), Bolotero® (Merz Aesthetik, Germany), Revanesse® (Auragenix Biopharma, Netherlands) and Rofilan Hylan Gel® (Cairo Tech, Egypt). Several of these crosslinked hyaluronic acids (e.g. Restylane) have been approved by the FDA as a soft tissue filling substance in clinical applications.

Another hydrogel suitable for use in the present disclosure is chitosan, which is a natural polysaccharide containing polymers of glucosamine and N-acetylglucosamine. Being a slowly biodegradable biomaterial and non-toxic to humans, chitosan has been extensively used as a pharmaceutical agent in the industry and research. Previously, modified chitosan has been used as a controlled release delivery system for hormones, drugs or proteins, wherein the release occurs both by diffusion and degradation of the biomaterial.

Other suitable natural hydrogel forming materials for use in the present disclosure are readily available to a person skilled in the art, and include, e.g., collagen, alginate, gelatin, fibrin, and agarose.

Synthetic hydrogels such as polyesters based on poly lactic acid (PLA), poly lactic glycolic acid PLGA, polycaprolactone (PCL) may also be used as hydrogels in the implants according to the embodiments of the present disclosure.

Depending on the material, it may be possible to achieve more adipogenesis or angiogenesis. By selecting different scaffold material or by material modifications (e.g. hyaluronan cross-linking), it may be possible to improve the adipogenic or angiogenic effect of the implant and focus the effect towards more angiogenic or more adipogenic potential.

An implant according to an exemplary embodiment may also include a mixture of hydrogels, such as a mixture of chitosan and hyaluronic acid. Hydrogels may be combined by blending, copolymerizing, or functionalizing.

In an exemplary embodiment, the biocompatible matrix may include nano- or microparticles. For instance, microparticles may be made from chitosan, e.g., by an iongelation method, or synthetic PLA, PLGA or PCL microparticles may be produced by a water-oil-water method, and be mixed inside a second hydrogel material, e.g., hyaluronic acid. In an exemplary embodiment, the adipose tissue extract may be provided in both the nano- or microparticles and the hydrogel surrounding the particles in an implant. In an exemplary embodiment, ATE may be combined with any degradable drug-release device.

In an exemplary embodiment, the amount of the biocompatible matrix in relation to the amount of the adipose tissue extract in the implant may be about 37% to about 50% biocompatible matrix and about 50% to about 63% extract. When the biocompatible matrix is a hydrogel, such as hyaluronic acid, a drop in the hydrogel content in the implant leads to a weaker gel structure, resulting in a faster degradation rate in the body. In an exemplary embodiment, the implant includes about 45.5% hyaluronic acid and about 54.5% adipose tissue extract. Such an implant has a gel strength weak enough to allow injection directly into the recipient tissue.

The hydrogel, or combinations thereof, may also be modified by cross-linking, freeze-drying, blending and/or copolymerisation, and different concentrations of hydrogel combinations may be used. The size of the implant may also vary from very small (few microlitres) to several tens of millilitres. In an exemplary embodiment for facial reconstruction purposes, 1 to 5 millilitres of the implant may be used.

The adipose tissue extract content in the implant may vary. In an exemplary embodiment, the implant includes between about 300 µg/ml to about 1.2 mg/ml of protein, for example, between 600 µg/ml and 1 mg/ml, and for example, close to 800 to 900 µg/ml.

The implant according to the present disclosure may be implanted by any suitable means. Injection offers a feasible method for implantation. Alternative forms of implantation are well known in the art, such as a scaffold, a film or a membrane.

The adipogenic and angiogenic potential of an implant according to the present disclosure was verified in animal experiments. The implants were implanted under rat skin in vivo, and the adipose tissue and blood vessel formation were monitored at the implantation site (Example 4, FIGS. 4A-4D and FIGS. 5A-5D). Already after two weeks, adipose tissue accumulation as well as vessel formation, were observed. At four to six weeks, extensive vessel formation and arterial-like structures were seen in close contact with the implant, as well as some adipose tissue formation. At 12 to 20 weeks, a highly vascularized, thick, dense layer of mature adipose tissue was detected at a close contact with the implant. At 40 weeks, the implant had degraded; however, developed mature adipose tissue was still present, substantiating long-lasting results obtainable with the implants of the present embodiments. Thus, these results demonstrate that the implant according to the present embodiments can indeed be used for soft tissue engineering and repair in vivo.

Thus, the present disclosure provides an implant which induces de novo adipose tissue formation and angiogenesis and provides a long-term delivery system of adipogenic and/or angiogenic factors that have been captured and immobilized into a hydrogel structure. The bioactive implant of the present disclosure aids in the induction of host cell infiltration and enables more efficient tissue regeneration. The effects of the implants are local and site-specific, reducing overall doses of adipogenic and angiogenic factors required for a certain effect. Not only is this cost-effective but also a way to avoid harmful systemic effects.

The present disclosure further provides a method of preparing an implant according to the present disclosure. The method includes mixing an adipose tissue extract with, or absorbing the same into, a biocompatible matrix. In an exemplary embodiment, the mixing may be performed carefully, avoiding air bubble formation, at room temperature in sterile syringes until ATE and the hydrogel material are completely mixed. The extract is immediately captured and absorbed into the hydrogel material and ready to be used for implantation.

Furthermore, the present disclosure provides the use of an adipose tissue extract and an implant according to the present disclosure in soft tissue repair or engineering. Accordingly, the extract and the implant may be used in a method of repairing or engineering soft tissue to achieve development of mature adipose tissue and adequate vascularization. In an exemplary embodiment, the implant is administered by injection.

Furthermore, the present disclosure provides the use of an adipose tissue extract and an implant according to the present disclosure in angiogenesis induction and/or ischemic tissue repair. Accordingly, the extract and the implant may be used in a method of repairing or engineering capillaries to achieve development of adequate vascularization. In an exemplary embodiment, the implant is administered by injection. In connection with an exemplary embodiment of the present disclosure, it has been shown, that for adipogenesis, usually the presence of existent fat cells or adipose tissue stem cells in a tissue is advantageous. If the implant is, e.g., administered into a tissue with no adipose cells, the effect of the implant may be more or mostly angiogenic rather than adipogenic.

One advantage of an exemplary embodiment of the present disclosure is that the preparation of ATE is easy and its tailoring is fast due to a short incubation time and short mixing time. Thus, the whole process of deriving an adipose tissue, processing it into an ATE and further into an implant, as well as implantation may be completed during one operation.

It will be obvious to a person skilled in the art that, as technology advances, the inventive concept can be implemented in various ways. The present disclosure and its embodiments are not limited to the examples described below but may vary within the scope of the claims.

Example 1

Preparation of Adipose Tissue Extracts for Cell Culture and Animal Studies

Human adipose tissue specimens obtained from liposuctions and as a subcutaneous tissue from surgical operations, as well as rat adipose tissue specimens obtained from sacrificed rats were minced into small pieces, if necessary. Tissue pieces or liposuction material was transferred into 50 ml tubes (Nunc). Sterile salt solution (for animal studies) or DMEM/F12 medium (for cell culture studies) without any supplements was added to the tubes and incubated for at least 45 minutes. The tubes were shaken gently a few times during the incubation. Samples of the adipose tissue extract (ATE) were collected at various time points (at each collection point, the medium or salt solution was completely removed and replaced with a fresh liquid), centrifuged at 12 000 rpm for 5 minutes and sterile filtered prior to use in cell culture or animal experiments. Viability of the cells was tested by isolating the cells and further culturing them after 24 hour of ATE production. The stromal vascular fraction cells were morphologically normal and had retained their biological activity and proliferated normally.

Eighty human ATE samples derived from different patients and/or collected at different time points (1 hr, 2 hr or 24 hr) were analyzed for a total protein concentration by a BCA protein Assay (Pierce Biotechnology, Rockford, Ill., USA). The total protein concentration was always at its highest at the time points 1 hr (1. aliquot) and 2 hr (2. aliquot), and the protein concentration decreased during the time (FIG. 1A). Typically, the total protein concentration was about 1.8 mg/ml to about 2.5 mg/ml in the first aliquot (1 hr), about 1.5 mg/ml in the second aliquot (2 hr), and about 1 mg/ml in the third aliquot (24 hr). Extracts incubated in a sterile salt solution or in a cell culture medium had corresponding total protein contents. Optimal protein production was achieved when equal volumes of an incubation solution (medium or sterile salt solution) and a minced adipose tissue were used for the extraction. Such conditions resulted in protein concentrations close to 2 mg/ml, which is in a proper range for cell culture studies. However, stronger concentrations may, and often have to be, diluted to a proper range. Any excess incubation solution resulted in too low protein concentrations that needed further modification by concentration in spin columns.

Furthermore, concentration of a vascular endothelial cell growth factor (VEGF), basic fibroblast growth factor (FGF-2) or insulin-like growth factor (IGF-1) was each measured in 31 to 40 human adipose tissue extract samples collected at different time points (1 hr, 2 hr and 24 hr) by Enzyme-Linked ImmunoSorbent Assay (ELISA, Quantikine Human VEGF Immunoassay, Quantikine Human FGF basic Immunoassay or Quantikine Human IGF-I Immunoassay, respectively, R&D Systems, Abingdon, UK). ELISA was performed according to the manufacturer's instructions. All standards and samples were measured in duplicate.

Figure 1B:
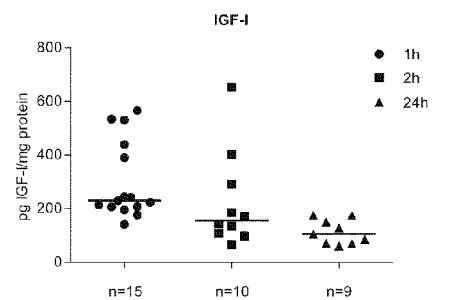
Figure 1C:
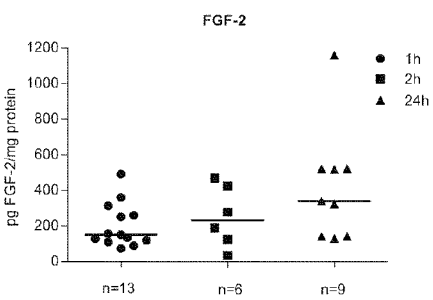
Figure 1D:
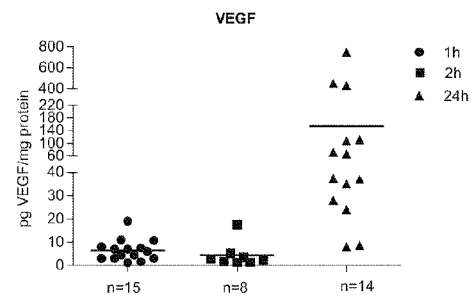
Figure 2A:
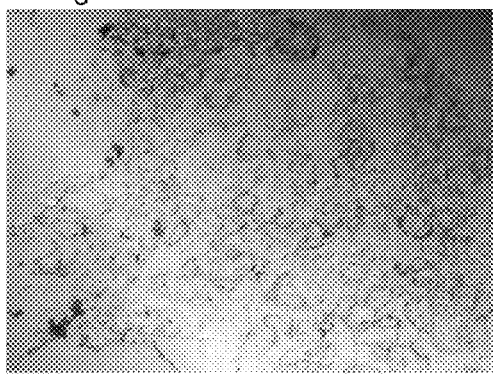
FIGS. 2A-2D illustrate adipogenic differentiation of human adipose stem cells (hASCs).
Figure 2B:
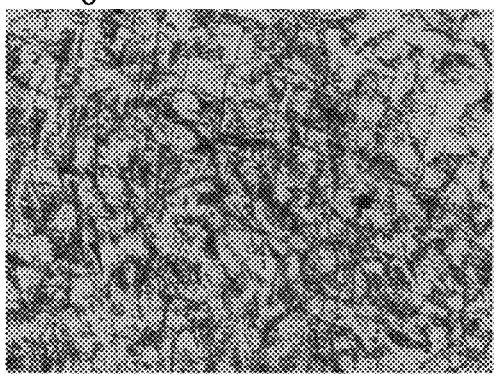
Figure 2C:
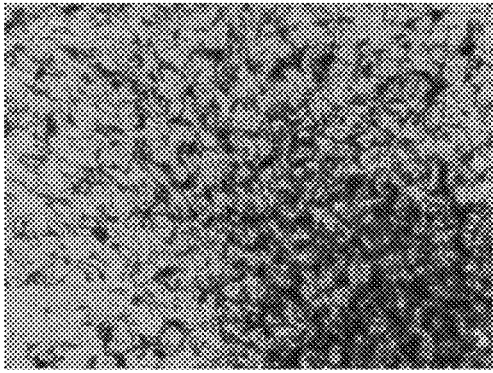
Figure 2D:
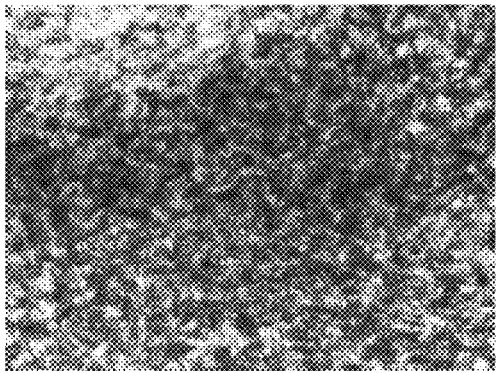
Figure 3A:
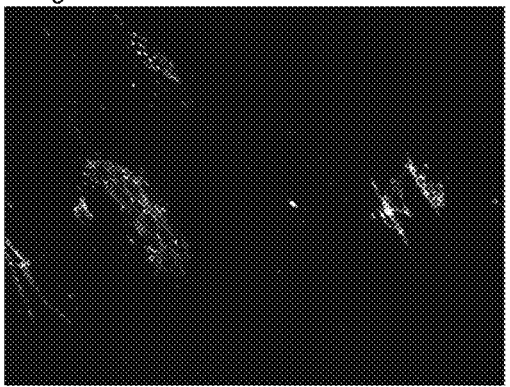
FIGS. 3A-3D demonstrate tube formation in an angiogenesis assay.
Figure 3B:
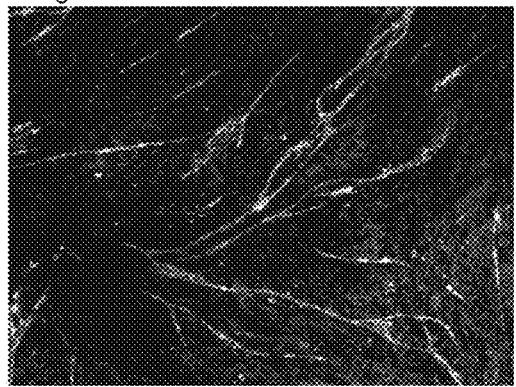
Figure 3C:
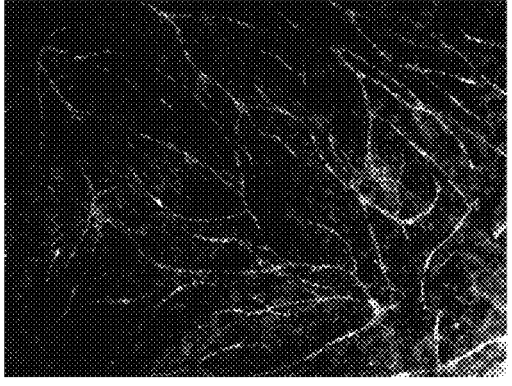
Figure 3D:
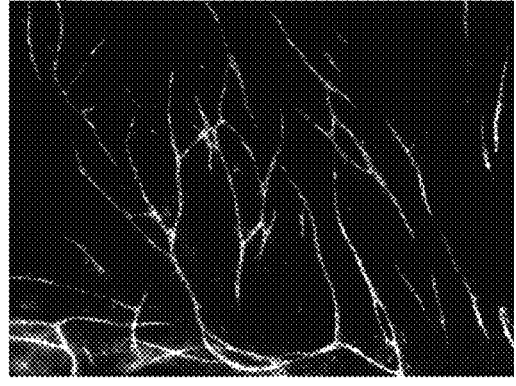
Figure 4A:
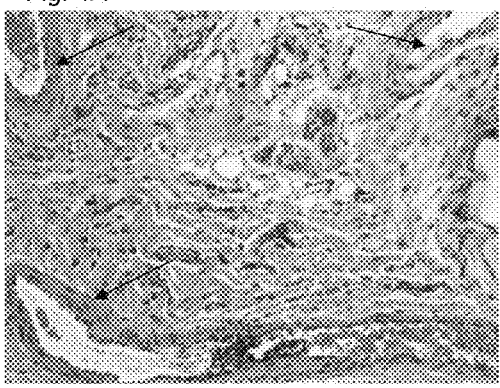
FIGS. 4A-4D illustrate vascularization and adipose tissue formation in vivo in rat subcutis at 2 weeks after implantation of an implant according to the present embodiments.
Figure 4B:
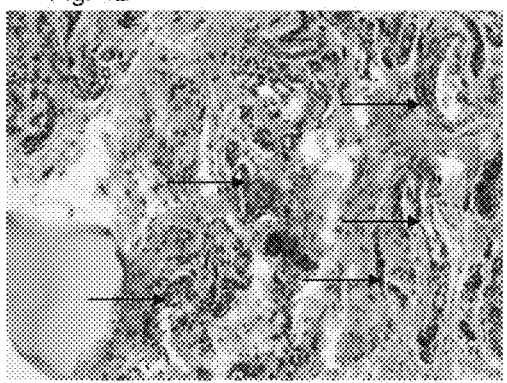
Figure 4C:
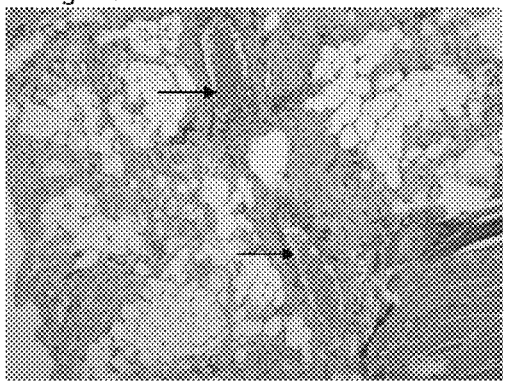
Figure 4D:
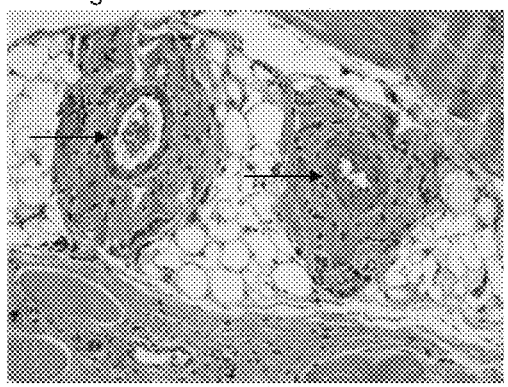
Figure 5A:
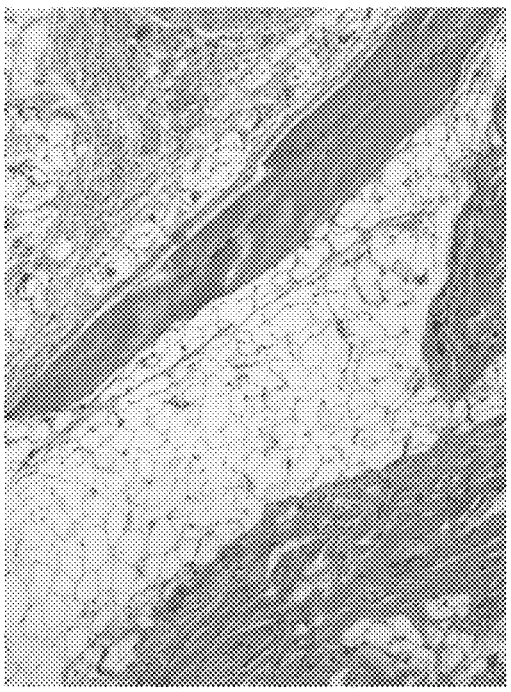
FIGS. 5A-5D illustrate massive adipose tissue formation at 12 weeks (FIGS. 5A and 5B) and 20 weeks (FIGS. 5C and 5D) after implantation of the implant according to the present embodiments. The implant is shown by arrows in FIGS. 5B and 5D.
Figure 5B:
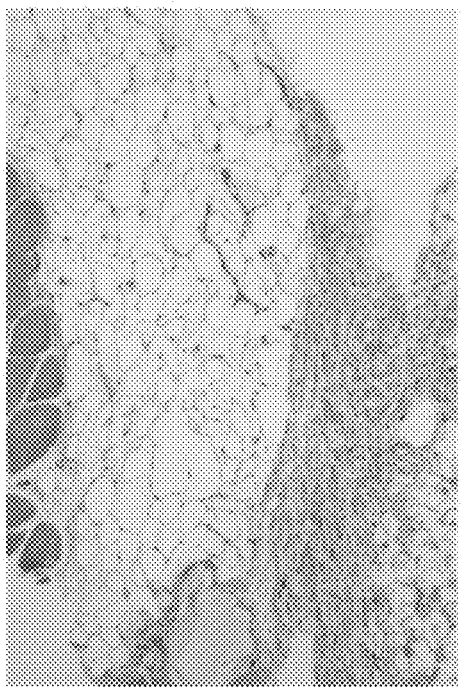
Figure 5C:
Figure 5D:

According to the results, IGF-1 concentration was at its highest level after 1-hour incubation (FIG. 1B), while FGF-2 concentration was quite high throughout the incubation (FIG. 1C). VEGF seemed to increase dramatically after 24 hours of culturing (FIG. 1D). Though the VEGF concentration was adequate at 1 hour and 2 hours for adipogenesis or angiogenesis induction as tested, VEGF reached very high levels only after a 24-hour incubation.

Furthermore, altogether 120 growth factors and cytokines were tested from two different extract samples at two different time points (1 hr and 24 hr) with RayBio® Human Cytokine Antibody Array C Series 1000 (RayBioTech, Inc., Norcross, Ga., USA). The array was performed according to the manufacturer's instructions. All samples were measured as duplicates and results obtained were semiquantitative. The factors that are shown as (−) in Table 1, were not expressed or their expression was low and thus undetectable in the array.

According to the cytokine measurements, the cytokine pattern of ATE within the limits of detection of the array was as follows: the 1 hr ATE samples expressed high amounts of angiogenin, adiponectin, TIMP-1 and TIMP-2, MIF, IGFBP-6, NAP-2, leptin, PDGF-BB, GRO and small amounts of several other factors, shown in Table I. The 24 hr ATE samples expressed high amounts of angiogenin, IL-6, NAP-2, MCP-1, adiponectin, GRO, TIMP-1, TIMP-2 and small amounts of several other factors, shown in Table I. At 24 hours, over all, more cytokines were expressed than at 1 hour (see Table I). Leptin, PDGF-BB, MIF, and IGFBP-6 expressions were high at 1 hour, whereas low at 24 hours. At 24 hours, MCP-1, IL-6, CCL5 and VEGF expression was high, but only detected in low amount at 1 hour.

Thus, by varying the incubation time and adjusting the growth factor concentrations, it is possible to prepare and tailor the ATE for different uses.

TABLE 1

Expression of various cytokines

| Cytokine | 1 Hour | 24 Hours | Cytokine | 1 Hour | 24 Hours |
|---|---|---|---|---|---|
| control | ++++ | ++++ | VEGF | + | +++ |
| FGF-2 | + | + | IGF-I | + | + |
| angiogenin | +++++ | +++++ | MIF | ++ | + |
| adiponectin(Acrp30) | ++++++ | ++++ | IGFBP-6 | +++ | − |
| TIMP-1 | +++ | +++ | NAP-2 | ++ | ++++ |
| TIMP-2 | +++ | +++ | leptin | ++ | + |
| CCL5 (RANTES) | + | ++ | PDGF-BB | ++++ | − |
| MCP-1 | + | ++++ | GRO | ++ | +++ |
| IL-8 | − | ++ | IL-6 | + | ++++ |
| IL-5 | − | ++ | AgRP | − | + |
| Fas/TNFRSF6 | − | + | angiopoietin-2 | − | + |
| MIP-1α | + | + | amphiregulin | − | + |
| IGF-1 SR | + | + | Axl | − | + |
| osteoprotegerin | + | + | GITR | − | + |
| MIP-1β | + | + | GITR-ligand | − | + |
| MIP-3β | − | + | FGF-9 | + | + |
| FGF-4 | + | + | ENA-78 | + | + |
| FGF-6 | + | − | EGF-R | − | + |
| GCSF | + | + | Dtk | − | + |
| IL-1 R4/ST2 | + | + | CTACK | − | + |
| IL-1 RI | + | + | ICAM-1 | − | + |
| IL-4 | − | + | | | |
| IL-11 | + | + | ICAM-3 | − | + |
| IL-12 p70 | + | + | IGFBP-3 | − | + |
| IL-12 p40 | − | + | PIGF | − | + |
| IL-17 | − | + | oncostatin M | − | + |
| TRAIL R3 | + | − | NT-4 | − | + |
| TRAIL R4 | − | + | SCF | + | + |
| uPAR | + | − | MSP-α | − | + |
| VEGF-D | + | − | lymphotactin | − | + |
| MCP-2 | − | + | I-TAC | − | + |
| MCP-3 | − | + | thrombopoietin | − | + |
| eotaxin-2 | + | − | LIGHT | + | + |
| eotaxin-3 | + | + | IL-1α | + | − |

Abbreviations: AgRP, agouti-related protein; Axl, AXL receptor tyrosine kinase; CCL5 (RANTES), chemokine (C-C motif) ligand 5; CTACK, cutaneous T cell-attracting chemokine; Dtk, growth factor receptor tyrosine kinase; EGF-R, epidermal growth factor receptor; ENA-78, epithelial neutrophil activating peptide-78; EGF-R, epidermal growth factor R; FGF-2, fibroblast growth factor 2; FGF-4, fibroblast growth factor 4; FGF-6, fibroblast growth factor 6; FGF-9, fibroblast growth factor 2; GCSF, granulocyte colony-stimulating factor; GITR, glucocorticoid-induced tumor necrosis factor receptor; GITR-ligand, glucocorticoid-induced tumor necrosis factor receptor ligand; GRO, cytokine-induced neutrophil chemoattractant 1 growth related oncogene; ICAM-1, intercellular adhesion molecule 1; ICAM-3, intercellular adhesion molecule 3; IGF-1, insulin-like growth factor 1; IGF-1 SR, insulin-like growth factor 1 soluble receptor; IGFBP-3, insulin-like growth factor binding protein 3; IGFBP-6, insulin-like growth factor binding protein 6; IL-1 R4/ST2, interleukin 1 Receptor 4; IL-1 R1, interleukin 1 Receptor 1; IL-5, interleukin 5; IL-6, interleukin 6; IL-8, interleukin 8; IL-11, interleukin 11; IL-12 p70, interleukin 12 p70; IL-12 p40, interleukin 12 p40; IL-17, interleukin 17; I-TAC, Interferon-inducible T-cell alpha chemoattractant; LIGHT, homologous to lymphotoxin, exhibits inducible expression, and competes with HSV glycoprotein D for herpes virus entry mediator, a receptor expressed by T lymphocytes; MCP-1, monocyte chemotactic protein-1; MCP-2, monocyte chemotactic protein-2; MCP-3, monocyte chemotactic protein-3; MIF, macrophage migration inhibitory factor; MIP-1α, macrophage inflammatory protein-1α; MIP-1β, macrophage inflammatory protein-1β; MIP-3β, macrophage inflammatory protein-3β; MSP-α, macrophage stimulating protein α; NAP-2, human neutrophil activating protein-2; NT-4, neurotrophin 4; PIGF, placenta growth factor; TIMP-1, tissue inhibitor of matrix metalloproteinase-1; TIMP-2, tissue inhibitor of matrix metalloproteinase-2; TRAIL R3, tumor necrosis factor-related apoptosis-inducing ligand receptor 3; TRAIL R4, tumor necrosis factor-related apoptosis-inducing ligand receptor 4; uPAR, urokinase-type plasminogen activator; VEGF, vascular endothelial growth factor; VEGF-D, vascular endothelial growth factor D.

Example 2

Adipogenic Potential of Adipose Tissue Extracts

Human adipose derived stem cells (hASC) were isolated according to a protocol modified from Zuk P A et al. (Mol Biol Cell. 2002 Dec;13(12):4279-95.). Briefly, human adipose tissue specimens obtained from surgical operations or liposuctions were cut into small pieces if necessary and digested enzymatically in DMEM/F12 medium supplemented with 0.05% collagenase I for 60 to 90 minutes at 37° C. in a shaker. To ease the digestion, the tissue was occasionally aspirated during the incubation period. In order to separate a stromal vascular fraction and a stem cell population, the digested tissue was centrifuged at 600×g for 10 minutes at room temperature. The digested tissue was first filtered through a filter having a pore size of 100 μm and then through a filter having a pore size of 40 μm. The human stem cell population obtained was cultured in DMEM/F12 supplemented with 15% human serum (HS, Cambrex), 1 mM L-glutamine, and 1% antibiotic-antimycotic mixture (Gibco). The cells were maintained at 37° C. under a 5% $CO_2$ air atmosphere at a constant humidity. The cells were allowed to attach over night. The next day, the cells were washed several times and the medium was changed to remove debris.

hASCs were cultured as above and the medium was changed every two to three days. Early passage (p1 to p5) confluent stem cell cultures derived from two or three different patients were trypsinized, pooled together and plated in a culture medium at a density of 10 000 cells/$cm^2$. The next day, six different culture conditions were applied:
  1) normal culture medium supplemented with human serum: DMEM/F12, 15% human serum, 1% antibiotic-antimycotic mixture, 1 mM L-glutamine;
  2) culture medium supplemented with ATE: DMEM/F12, 15% human serum 1% antibiotic-antimycotic mixture, 1 mM L-glutamine; and 300 μg/ml (protein concentration) of ATE (approximately 25% of the culture volume)
  3) culture medium supplemented with ATE: DMEM/F12, 15% human serum 1% antibiotic-antimycotic mixture, 1 mM L-glutamine; and 600 μg/ml (protein concentration) of ATE (approximately 50% of the culture volume)
  4) culture medium supplemented with ATE: DMEM/F12, 15% human serum 1% antibiotic-antimycotic mixture, 1 mM L-glutamine; and 950 μg/ml (protein concentration) of ATE (approximately 75% of the culture volume)
  5) ATE (1200 μg/ml protein concentration; 83% of the final culture volume) supplemented with 15% human serum, 1% antibiotic-antimycotic mixture, 1 mM L-glutamine;
  6) adipogenic medium: DMEM/F12, 10% fetal bovine serum (FBS), 1% antibiotic-antimycotic mixture, 1% L-glutamine, 33 M biotin, 17 M pantothenate, 100 nM insulin, 1 M dexamethasone (Sigma), and 0.25 mM isobutylmethylxanthine (IBMX, Sigma). IBMX was left in the adipogenic culture medium for the first 24 hours only.

The medium was changed every two to three days. At defined time points (2 to 3 weeks and 5 weeks) the adipogenic differentiation was evaluated by staining the cell cultures with Oil-red-O (Sigma). Cell culture reagents were obtained from Gibco unless otherwise stated.

Adipogenic differentiation in the different culture conditions was assessed based on triglyceride accumulation in the cells detected by Oil-red-O staining. Briefly, 0.5% Oil-red-O solution was prepared by dissolving Oil-red-O in 100% isopropanol. The solution was mixed with distilled water in a ratio of 2:3 and left at room temperature for 10 minutes. The resulting solution was filtered using a standard filter paper. Before staining, the cell culture media were aspired from the wells and the wells were rinsed gently with PBS two to three times. The cells were fixed with 4% paraformaldehyde solution for 20 minutes. The wells were then rinsed with distilled water. The cells were incubated in 60% isopropanol solution for 2 to 5 minutes, after which previously prepared Oil-red-O solution was added and incubated for 5 minutes. The wells were rinsed with distilled water until the water was clear. Phase contrast micrographs of the stained cells were taken with Nikon TS-100 connected to a CCD camera unit (Nikon, Tokyo, Japan). The amount of adipogenic differentiation was measured by evaluating the extent of red-stained area within the cells.

In each stem cell population, the adipose tissue extract was shown to induce a dose-dependent homogenic adipogenic conversion to a majority of the cells in the culture after 1 to 3 weeks in culture (FIG. 2). The adipogenic effect was seen when at least 200 μg/ml of ATE was used, and the adipogenic effect was more extensive when higher concentrations of ATE were tested, up to 2 mg/ml. The ATE used in the experiment was prepared as described in Example 1, and contained 1.8 mg/ml protein, 143 pg/ml IGF-I, 123 pg/ml FGF-2, and 3.6 pg/ml VEGF.

Example 3

Angiogenic Potential of Adipose Tissue Extracts

BJ fibroblasts (CRL-2522; American Type Culture Collection, Manassas, Va., USA,) were cultured in MEM (Gibco) supplemented with 10% fetal bovine serum, 1% L-glutamine, 1% non-essential amino acids (Gibco), and 1% antibiotic-antimycotic mixture (Gibco). The cells were maintained at 37° C. under a 5% CO2 air atmosphere at a constant humidity. The medium was changed every two to three days and confluent cells were split 1:4.

Human umbilical vein endothelial cells (HUVEC) were isolated from an umbilical cord specimen and cultured in Endothelial Growth Medium (EGM-2, Lonza) up to passage 7. The cells were maintained at 37° C. under a 5% $CO_2$ air atmosphere at a constant humidity. The medium was changed every two to three days and confluent cells were split 1:4.

To study the angiogenic potential of the adipose tissue extract according to the present disclosure, BJ fibroblasts were plated at a density of 20000 cells/$cm^2$ into 48-well plates and cultured to confluency (3 to 4 days). Next, the HUVECs were plated on top of confluent fibroblast cultures at a density of 4000 cells/$cm^2$. Upon plating the HUVECs, the culture medium was changed to EGM-2 medium (from EGM-2 bullet kit, Lonza). The next day, parallel co-cultures were treated differently:
  1) Negative control: Endothelial cell basal medium (EBM-2, from the EGM-2 bullet kit);
  2) Positive control A: EBM-2 supplemented with 10 ng/ml VEGF (R&D Systems) and 1 ng/ml FGF-2 (Sigma);
  3) Positive control B: EBM-2 supplemented with 50 ng/ml VEGF (R&D Systems) and 5 ng/ml FGF-2 (Sigma);

4) EBM-2 supplemented with 440 μg/ml (protein concentration; approximately 25% of the total volume of cell culture medium) of ATE;

5) EBM-2 supplemented with 880 μg/ml (protein concentration; approximately 50% of the total volume of cell culture medium) of ATE;

6) EBM-2 supplemented with 1320 μg/ml (protein concentration; approximately 75% of the total volume of cell culture medium) of ATE.

All culture media were supplemented with 2% FBS, 1% L-glutamine, 0.1% GA-1000 (solution of gentamicin sulfate and amphotericin B from the EGM-2 bullet kit). ATE used in the experiment was prepared as described in Example 1 and contained 1.76 mg/ml protein, 143.4 pg/ml IGF-I, 123.1 pg/ml FGF-2, and 3.56 pg/ml VEGF.

The cells were cultured for seven days prior to immunocytochemical staining with an endothelial cell specific antibody (anti-von Willebrand factor). The media were changed once during the culture.

Immunocytochemical staining was performed as follows: Cells were washed three times with PBS, fixed with ice-cold 70% ethanol for 20 minutes, permeabilized with 0.5% Triton X-100 (J T Baker, Phillipsburg, N.J., USA) for 15 minutes, and blocked for unspecific staining with 10% BSA (Gibco) for 30 minutes. After blocking, the cells were incubated with a von Willebrand Factor primary antibody (anti-vWF produced in rabbit, Sigma, 1:500) at 4° C. overnight. The next day, cells were washed three times with PBS, incubated for 30 minutes with a secondary antibody (polyclonal Antibody to Rabbit IgG FITC, Acris Antibodies GmbH, Hiddenhausen, Germany, 1:500), and washed three times with PBS. After staining, 500 μl of PBS was left into the cell culture wells and the wells were sealed with parafilm. Fluorescence was visualized by Nikon Eclipse TS100 microscope (Nikon, Tokyo, Japan) equipped with Nikon DS Camera Control Unit DS L-1, and images were processed with Adobe Photoshop software (Adobe Systems, San Jose, Calif., USA).

The adipose tissue extract induced a formation of tube-like structures in the co-cultures from day 4 or 5. After seven days, a clear tube formation was observed in positive controls A and B (FIGS. 3E and 3F, respectively) and in cells treated with 880 μg/ml (FIG. 3C) or 1320 μg/ml (FIG. 3D) of ATE. Growth factor treatment in positive control A clearly stimulated the formation of typical long, thin, branched capillary like structures. Any excess amount of growth factors in positive control B, however, resulted in somewhat disorganized or clustered tube structures. Growth factor treatment in positive control A represented an in vivo situation in a tissue. The results obtained with 1320 μg/ml of ATE, and even with 880 μg/ml of ATE, were very similar to the results obtained with known angiogenic growth factors (positive control A). The adipose tissue extract produced a dose-dependent effect on the HUVEC cells and produced a network of capillaries.

Example 4

Preparation of Injectable Implants

Two different injectable implants according to the present disclosure were formulated for animal studies: 1) an implant including 54.5% rat ATE (total protein concentration 1.3 mg/ml) and 45.5% hyaluronic acid; and 2) an implant including 54.5% human ATE (total protein concentration 2.5 mg/ml) and 45.5% hyaluronic acid. In these formulations, the hyaluronic acid used was a non-animal derived stabilized hyaluronic acid (NASHA) 20 mg/ml, Restylane (Q-Med, Uppsala, Sweden). Different forms of crosslinked hyaluronic products (e.g. Restylane Perlane or Restylane Touch or Macrolane) may also be used, depending on the type of the defect.

Implants were prepared by mixing 1 ml of Restylane carefully with 1.2 ml of ATE (prepared as described in Example 1). The final implant volume placed under subcutis of rats was always 100 μl and consisted of 45.5 μl of hyaluronic acid and 54.5 μl of incorporated liquid. Such implants are viscous enough to avoid immediate resorption into a tissue or leakage from an injection site, but contain a high amount of the extract.

Control implants containing 54.5% phosphate buffered saline (PBS) and 45.5% hyaluronic acid were prepared as described above.

In order to study protein release from the implants, 120 μl of each implant was injected into a 96-well plate strip insert with a pore size of 0.2 μm (Nunc). The inserts were placed into 96-well cell culture plates and incubated in 150 μl of PBS at 37° C. for several weeks. The PBS was changed every three days. Aliquots were collected and stored at −20° C. for total protein and ELISA analysis. The control implants released no protein, whereas the ATE containing implants released a maximum of 350 μg/ml of protein per three days and a minimum of 100 μg/ml of protein per three days during a two week period. This release experiment showed that protein is released from the implant and, therefore, the implants are functional.

Example 5

Adipogenic and Angiogenic Activity of Implants In Vivo (Animal Studies)

All animal experiments were performed according to the Finnish animal protection laws and approved by the Department for Social Welfare and Health Services of State Provincial Office of Western Finland.

Twenty-seven male Sprague-Dawley rats (average weight 300 g) were anesthesized with a mixture of Domitor (1 mg/ml; 0.5 mg/kg) and Ketalar (10 mg/ml; 75 mg/kg). Implants and controls prepared as described in Example 4 were injected under dorsal subcutis of the rats with a 1 ml syringe and a 27 gauge needle in a final volume of 100 μl. Implants were left under subcutis for 1, 2, 3, 4, 6, 8, 12 or 20 weeks and for 9 months, after which the animals were sacrificed with carbon dioxide. Tissue samples were taken from the implantation sites and processed for histological analysis. The human ATE used in the experiment was prepared as described in Example 1 and contained 2.5 mg/ml protein, 200 pg/ml IGF-1, 863 pg/ml FGF-2, and 61 pg/ml VEGF. The Rat ATE used in the experiment was prepared as described in Example 1 and contained 1.3 mg/ml protein.

The tissue samples were fixed in 4% paraformaldehyde overnight, dehydrated with a graded ethanol series and embedded in paraffin. Specimens were cut into 5 μM thick slices with microtome (Microm HM 430, Microm GmbH, Waldorf, Germany) and stained with hematoxylin-eosin (H&E) for histological analysis. Images were taken with a Nikon Microphot FXA microscope (Nikon, Tokyo, Japan) and processed using Corel Draw 10 and Adobe Photoshop 7.0.

Hematoxylin-eosin staining of the histological specimens revealed neovascularization and adipose tissue formation in the implant area (FIG. 4 and FIG. 5). Numerous small vessels and some mature large vessels with erythrocytes present were detected in samples taken after 2 weeks after the implantation. Only little or no adipose tissue formation was detected.

In the samples taken 4 weeks after the implantation, some white round adipose tissue deposits in close contact with the remaining implant and with the formed vessel structures were detected. The small size of the adipose tissue deposits detected indicated that they were newly formed. In the samples taken 4 or 6 weeks after the implantation, vascularization had proceeded, and a massive number of small vessels and structures similar to arterioles and venules could be seen, as well as some adipose tissue formation. The vessels formed were larger in number as well as in diameter, when compared to the controls. At 12 to 20 weeks, a highly vascularized, thick, dense layer of mature adipose tissue was detected in close contact with the implant.

In the experiment, inflammation reactions, implant degradation rate, adipogenesis and angiogenesis were followed up to nine months. There were no complications due to the implant injection procedure or postoperative recovery from the anesthesia. No inflammation or capsule formation was detected. All implants and controls induced some small vessel formation possibly due to a mild reaction caused by the foreign hyaluronic acid material. However, vessel formation was extensive only in rats injected with implants containing rat and human ATE. The human ATE produced more vascularization in rat than the rat ATE but they both seemed to induce adipogenesis well.

Example 6

Clinical Pretrial

Human adipose tissue extract was prepared from a liposuction sample by direct suction into a sterile syringe. To maximize protein extraction, 2.5 ml of the liposuctioned fat was mixed with 1.5 ml of sterile isotonic salt solution in a sterile syringe and incubated for 45 minutes in room temperature. The syringe was shaken several times during incubation. The total protein concentration of the resulting extract was 2.5 mg/ml, and growth factor concentrations were 17 pg/ml VEGF and 177 pg/ml FGF-2.

After the incubation, the extract was sterile filtered through a 0.2 μm filter (Acrodisc syringe filter, Pall Gelman Laboratory, An Arbor, USA) into a second sterile syringe connected via an adapter to the first syringe. The second syringe now containing the extract was connected with an adapter to a third sterile syringe containing adequate amount of Restylane. The resulting sterile adipose tissue extract was mixed with Restylane, the ratio being 0.9 ml (45.5%) of Restylane and 1.2 ml (54.5%) of the adipose tissue extract. The liquid and gel phases were mixed by injecting the material back and forth between the second and the third syringes. The implant material was considered to be homogenous enough, when the pale pink color of the adipose tissue extract was suspended evenly in the material. The final implant contained 1.2 mg/ml protein.

The implant obtained was immediately injected with a 30 G needle subcutaneously into two different sites in a leg of a healthy volunteer. The first site included old, existing scar tissue, and 450 μl of the implant was injected therein. The second site in the leg was provided with two defects by removing subcutaneous fat tissue, such that the resulting round defect sites in the tissue were approximately 1 cm in diameter. One defect was left intact, as a control, whereas the other defect was filled with 900 μl of the implant.

Figure 6D:
FIGS. 6A-6D illustrate a clinical pretrial showing human subcutis and its adipose tissue formation and vascularization after implantation the implant according to the present embodiments beneath an old scar tissue in a leg.
Figure 6C:
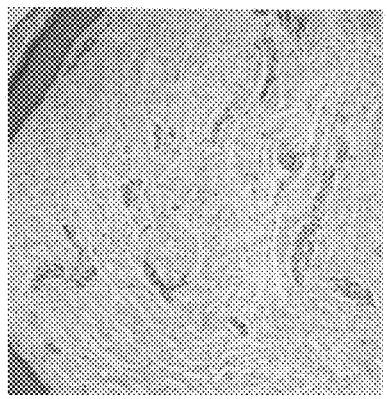
Figure 6B:
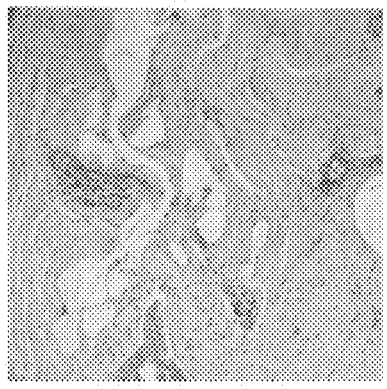
Figure 6A:
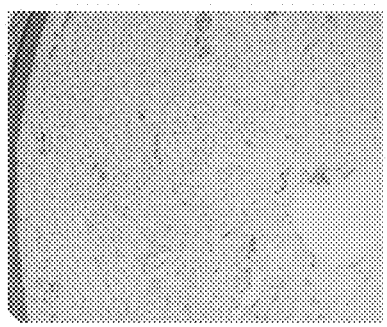

No allergic reactions or other complications were observed after implantation or during the follow-up time. Biopsies were taken from the implant sites as well as from the control tissue 3 months (12 weeks) and 6 months (28 weeks) after the onset of the pretrial. No inflammation reactions could be seen, and after three months, large amount of the implant material was still present. Increased blood vessel formation was seen in the scar tissue after the implantation. However, no excess adipose tissue formation was yet present. At six months (FIG. 6C), the tissue volume in dermis was greatly expanded compared to control, and a normal, highly vascularized loose connective tissue could be seen. In control (FIG. 6A), very few blood vessels can be seen. At 6 months, at the lower part of the dermis, excess blood vessel (arteriole-like vessel) formation was seen (b=blood vessels), and newly formed fat tissue (a=adipose tissue) was also present (FIG. 6C). According to the clinical pilot study, the material is extremely well tolerated, induces adipose tissue and blood vessel formation and the newly formed tissue is also present even after the implant itself has degraded.

Thus, the present disclosure provides an implant which induces de novo adipose tissue formation and angiogenesis, and provides a long-term delivery system of adipogenic and angiogenic factors that have been captured and immobilized into a hydrogel structure. The bioactive implant of the present disclosure aids in the induction of host cell infiltration and enables more efficient tissue regeneration. The effects of the implants are local and site-specific, reducing overall doses of adipogenic and angiogeninc factors required for a certain effect. Not only is this cost-effective but also a way to avoid harmful systemic effects.

Thus, it will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A cellfree adipose tissue extract, comprising: VEGF, FGF-2, and IGF-1 of small adipose tissue pieces containing viable cells, wherein a ratio of IGF-1 to FGF-2 is between 2:1 to 1:2, and a ratio of VEGF to FGF-2 is between 1:100 to 1:10, and wherein the cellfree adipose tissue extract is obtained without cell culturing.

2. The extract according to claim 1, wherein the growth factor content per 1 mg of total protein is at least 1 pg of VEGF, at least 70 pg of FGF-2, and at least 50 pg of IGF-1.

3. The extract according to claim 2, wherein the VEGF content per 1 mg of total protein is at least 7 pg.

4. The extract according to claim 2, further comprising angiogenin, adiponectin, TIMP-1 and TIMP-2, MIF, IGFBP-6, NAP-2, leptin, PDGF-BB and GRO.

5. The extract according to claim 2, further comprising angiogenin, IL-5, IL-6, IL-8, CCL5, NAP-2, MCP-1, adiponectin, GRO, TIMP-1, and TIMP-2.

6. The extract according to claim 1, the extract adapted for use in soft tissue repair or engineering, in wound healing, in treating burn injuries or in treating ischemic conditions.

7. The extract according to claim 2, the extract adapted for use in soft tissue repair or engineering, in wound healing, in treating burn injuries or in treating ischemic conditions.

8. An implant comprising a cellfree adipose tissue extract according to claim 1 and a biocompatible matrix.

9. An implant comprising a cellfree adipose tissue extract according to claim 2 and a biocompatible matrix.

10. The implant according to claim 8, wherein the biocompatible matrix is a hydrogel.

11. The implant according to claim 10, wherein the hydrogel is selected from a group consisting of hyaluronic acid, chitosan, fibrin, collagen, alginate, polyesters based on poly lactic acid, poly lactic glycolic acid, polycaprolactone, and mixtures thereof.

12. The implant according to claim 8, which is injectable.

13. The implant according to claim 8, wherein the extract is allogenic.

14. The implant according to claim 8, the implant adapted for use in soft tissue repair or engineering, in wound healing, in treating burn injuries or in treating ischemic conditions.

15. A method of preparing the cellfree adipose tissue extract according to claim 1 comprising a predetermined amount of VEGF, FGF-2, and IGF-1, the method comprising the following steps:
   a) providing a non-homogenized adipose tissue sample comprising viable cells,
   b) incubating the sample a predetermined time, and
   c) collecting the extract the method excluding a step of cell culturing.

16. The method of claim 15, wherein the growth factor content per 1 mg of total protein is at least 1 pg of VEGF, at least 70 pg of FGF-2, and at least 50 pg of IGF-1.

17. A cellfree adipose tissue extract obtained by the method according to claim 15.

18. A method of preparing an implant according to claim 8, the method comprising mixing the adipose tissue extract with, or absorbing the same into, the biocompatible material.

19. A method of inducing adipogenesis, the method comprising implanting into a subject in need thereof an implant according to claim 8.

20. A method of inducing angiogenesis, the method comprising implanting into a subject in need thereof an implant according to claim 8.

* * * * *